United States Patent [19]

Kaiser

[11] Patent Number: 4,963,193
[45] Date of Patent: Oct. 16, 1990

[54] OXO-IONYL ESTERS USEFUL AS TOBACCO FLAVORANTS AND TOBACCO PRODUCTS CONTAINING SAME

[75] Inventor: Roman Kaiser, Uster, Switzerland

[73] Assignee: Givaudan Corporation, Clifton, N.J.

[21] Appl. No.: 776,555

[22] Filed: Sep. 16, 1985

[30] Foreign Application Priority Data

Sep. 21, 1984 [CH] Switzerland .......................... 4523/84

[51] Int. Cl.$^5$ .......................... A24B 3/12; A24B 15/32
[52] U.S. Cl. .................................................. 131/276
[58] Field of Search ................................ 131/276, 277

[56] References Cited

FOREIGN PATENT DOCUMENTS 56-57734 5/1981 Japan .
57-26637 2/1982 Japan .

OTHER PUBLICATIONS

Acta Chemica Scandinavica, Band 27, Nr. 6, 1973, Seiten 2107–2114, Copenhagen, DK.; A. J. Aasen et al.
Helvetia Chimica Acta, Band 65, Nr. 6, 1982, Seiten 1927–1928, Basel, CH; S. Katsumura et al.
Chemical Abstracts, Band 75, Nr., 26, 6 12/1971 vol. 75, No. 23.
A. J. Aasen et al., Acta Chem. Scand. 27, (1973), 2107–2114.
S. Katsumura et al., Helv. Chim. Acta 65, (1982) 1927.
A. J. Aasen et al., Acta Chem. Scand. B28 (1974) 285–288.
F. Kienzle et al., Helv. Chim. Acta 58, (1975) 27–40.
H. Ide et al., Biochem. J. 119 (1970) 281–287.
R. Kaiser et al., Helv. Chim. Acta 61 (1978) 2328–2335.

Primary Examiner—V. Millin
Attorney, Agent, or Firm—Robert F. Tavares; Linda A. Vag

[57] ABSTRACT

Tobacco products, tobacco flavoring compositions, and methods for improving, modifying or enhancing the organoleptic properties of tobacco products, which comprise adding thereto an effective amount of an oxo-ionyl ester of the formula

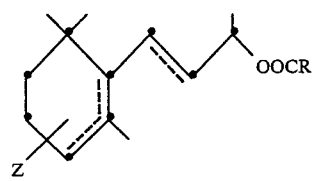

I wherein:
RCO represents an acyl group containing from one to eighteen carbon atoms,
the dotted line in the side-chain represents an optional bond,
one of the dotted lines in the ring represents an additional bond, and,
Z represents an oxo group which is in the position α to the double bond in the ring, said amount being effective to modify the organoleptic properties of said tobacco product or composition.

18 Claims, No Drawings

OXO-IONYL ESTERS USEFUL AS TOBACCO FLAVORANTS AND TOBACCO PRODUCTS CONTAINING SAME

BACKGROUND OF THE INVENTION

Manufacturers of tobacco products expend a considerable effort to provide to the consumer product which is uniform and which has a pleasant and distinctive flavor and aroma both before and during smoking.

The characteristic aroma and flavor were traditionally obtained by blending domestic, oriental and turkish tobaccos, each of which contributes its own particular characteristics and nuances to the final blend. The supply of the particular tobaccos needed to supply these characteristic nuances is, however, often subject to the vagaries common to agricultural products such as poor crop years, price instability, political turmoil, etc.

In order to alleviate the impact of such problems there have been developed a number of tobacco flavor additives to enhance, improve or modify the organoleptic properties of the tobacco blends. Such additives are used both to restore desirable characteristics of flavor, aroma and smoke that may be lacking for one reason or another, or to provide a distinctive note to the product. A number of additives used in the art are discussed by Sidney Gutcho in Tobacco Flavoring Substances and Methods, Noyes Data Corporation, Park Ridge, N.J. (1972).

At present there is a demand for cigarettes with low nicotine content (light cigarettes, lights, low-delivery cigarettes, low tar cigarettes). The results desired can be achieved, for the most part, by means of a so-called high-retention filter and/or ventilation. Certain aromatic substances may be lost through filtering or the ventilation process. It is therefore highly desirable to compensate for these losses by developing new tobacco flavor additives which can contribute a full-bodied tobacco character to the smoke flavor of the tobacco product.

THE INVENTION

It has been found that the organoleptic properties of tobacco products can be improved by adding thereto an oxo-ionyl ester of the formula

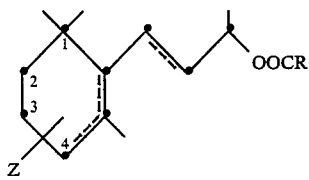

wherein:
RCO represents an acyl group containing one to eighteen carbon atoms,
the dotted line in the side-chain represents an optional bond,
one of the dotted lines in the ring represents an additional bond, and,
Z represents an oxo group which is in the position α to the double bond in the ring.

Formula I is intended to represent all possible stereoisomers and mixtures thereof.

The esters represented by formula I possess organoleptic properties which make them especially suitable for intensifying, improving, enhancing or modifying the organoleptic properties of tobacco products. Their addition to a tobacco product is found to contribute greatly to the smoke characteristics of the product particularly by intensifying the general tobacco impression and rounding-off the total tobacco flavor.

DESCRIPTION OF THE PREFERRED EMBODIMENTS

The acyl group RCO, as defined by formula I, may represent:
formyl,
alkanoyl containing from two to eighteen carbon atoms including acetyl, propionyl, butyroyl, valeroyl, isovaleroyl, and stearoyl,
alkanoyl containing from three to eighteen carbon atoms and one or more double bonds including crotonyl, linoleoyl, linolenoyl and oleoyl,
arylalkanoyl containing from seven to eighteen carbon atoms such as phenylalkanoyl (e.g. phenylacetyl).

Preferred esters are those in which the acyl group contains up to five carbon atoms. Among the preferred esters of formula I are:

(a) 4-oxo-β-ionyl valerate
 [4-(2,6,6-trimethyl-3-oxocyclohex-1-en-1-yl)but-3-en-2-yl valerate]
(b) 4-oxo-β-ionyl isovalerate
 [4-(2,6,6-trimethyl-3-oxocyclohex-1-en-1-yl)but-3-en-2-yl isovalerate]
(c) 4-oxo-β-ionyl butyrate
 [4-(2,6,6-trimethyl-3-oxocyclohex-1-en-2-yl)but-3-en-2-yl butyrate]
(d) 4-oxo-β-ionyl acetate
 [4-(2,6,6-trimethyl-3-oxocyclohex-1-en-1-yl)but-3-en-2-yl acetate]
(e) 4-oxo-β-ionyl formate
 [4-(2,6,6-trimethyl-3-oxocyclohex-1-en-1-yl)but-3-en-2-yl formate]
(f) 4-oxo-β-ionyl crotonate
 [4-(2,6,6-trimethyl-3-oxocyclohex-1-en-1-yl)but-3-en-2-yl crotonate]
(g) 4-oxo-dihydro-β-ionyl valerate
 [4-(2,6,6-trimethyl-3-oxocyclohex-1-en-1-yl)but-2-yl valerate]
(h) 4-oxo-dihydro-β-ionyl acetate
 [4-(2,6,6-trimethyl-3-oxocyclohex-1-en-1-yl)but-2-yl acetate]
(i) 3-oxo-β-ionyl valerate
 [4-(2,6,6-trimethyl-4-oxocyclohex-2-en-1-yl)but-3-en-2-yl valerate]

It can generally be said that the addition of an oxo-ionyl ester of formula I to a tobacco product improves its smoking characteristics. In particular, the general tobacco impression is intensified. The total flavor can become more fuller and additionally enriched organoleptically.

The type and extent of the improvement depends on the particular ester utilized For example, the (smoke) flavor of cigarettes treated with 4-oxo-β-ionyl valerate exhibits the typical aspects of dark tobacco and in total is substantially more rounded and more full. When 4-oxo-β-ionyl acetate is used, there can be established, in particular, a general intensification of the tobacco character and the additional appearance of flowery, spicy and tea-like aspects. Moreover, other compounds of formula I can yield, upon smoking, desirable novel, caramel-like, fruity, woody or sweet-flowery aspects or can enrich the total impression by giving rise to a highly desirable "salivating effect".

The term "tobacco product" is meant to include not only tobacco (e.g. Burley, Maryland, Virginia, Kentucky oriental types or mixtures thereof) itself, but also tobacco byproducts such as reconstituted and homogenized leaf and stem, tobacco surrogate (e.g. lettuce and cabbage leaf, etc.), and materials which are used in the processing of tobacco such as paper, filters, etc. Cigarette tobacco, cigar tobacco, chewing tobacco and pipe tobacco, etc. fall under the term "tobacco product".

The fact that the compounds of formula I are not highly volatile and the flavor-active compounds are released especially upon smoking confers advantages with respect to the flavor constancy and stability of the finished product. The compounds which are usually used for the flavoring of tobacco are frequently relatively volatile so that it is necessary upon storing the flavored tobacco products for an extended period of time to make allowance for a certain loss of flavor. This disadvantage can be largely prevented by using compounds of formula I.

The amount of ester of formula I which is conveniently added can depend on various factors, including the desired effect, the nature and the amount of other simultaneously used additives and/or the personal preferences of the flavorist. Amounts as low as 10 ppm based on the weight of the tobacco have been found to be effective, while amounts as high as 10,000 ppm have been found to be usuable. It is especially preferred, however, to use amounts in the range of 50 ppm to 2.000 ppm.

It is understood that the levels suggested above are merely suggestive of the preferred amounts and that they are always subject to the skill of the flavorist and the effect he seeks to achieve.

The manufacture of flavoring compositions for the flavoring of tobacco can be carried out by simply dissolving compounds I in a suitable solvent, especially a polar solvent such as alcohol, propylene glycol, etc., along with any additional odorants and/or flavorants and water, if desired, whereby the concentration of the compound I can amount to, for example, 0.5 to 50%.

The compounds I can be added to or admixed with the tobacco product (cigarettes, etc.) for example, in the form of the above flavoring compositions according to methods which are known to a person skilled in the art, such as spraying, atomization, immersion, coating, etc.

With the exception of the acetates, the compounds of formula I are novel compounds. Accordingly, the novel compounds of formula I also form an object of the present invention.

The compounds I can be obtained in a manner known per se, by esterifying oxo-ionols of the formula

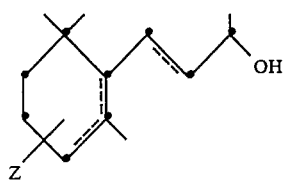

II wherein:
the dotted line in the side-chain represents an optional bond,
one of the dotted lines in the ring represents an additional bond, and,
Z represents an oxo group which is in the position α the double bond in the ring.

The esterification of the oxo-ionols II can be carried out in a manner know per se using usual acylating agents, e.g. acyl halides, especially the chlorides, or acid anhydrides. The procedure using the acid anhydride is preferred. The esterification is conveniently carried out in the presence of a base, e.g. an organic amine such as pyridine or dimethylaniline, and, if desired, using an inert solvent, e.g. a hydrocarbon or an ether, e.g. hexane, cyclohexane, toluene, diethyl ether, etc. A suitable temperature range is that of about 20° C.–80° C. see also Organikum, Org. Chem Grundpraktikum VEB Deutscher Verlag der Wissenschaften, Berlin (1977), pages 499 et seq.

ILLUSTRATION OF THE PREFERRED EMBODIMENTS

The following examples are included to illustrate the preferred embodiments of this invention and should not be construed as limiting. They are intended to embrace any equivalents or obvious extensions which are known or should be known to persons skilled in the art.

EXAMPLE 1

3.26 g (0.032 mol) of acetic anhydride are treated while stirring with 1.83 g (0.040 mol) of formic acid, the mixture is held at 60° C. for 30 minutes, then cooled to 0° C., 5.00 g (0.024 mol) of 4-oxo-β-ionol are added dropwise and the mixture is subsequently stirred at 0° C. for 16 hours and at room temperature for one hour. For the working-up, the mixture is treated with 50 ml of hexane, the organic phase is washed in each case twice with water, soda solution and again with water, dried with sodium sulphate and the filtered solution is concentrated. Bulb-tube distillation of the crude product (5.2 g) gives 4.5 g of >93% 4-oxo-β-ionyl formate. B.p. about 110° C./0.05 mmHg.

IR: 1720, 1667, 1600, 1175, 1040, 970 cm$^{-1}$.

NMR: 1.13 (2s, 6H); 1.42 (d, J=6.5, 3H); 1.80 (s, 3H); 1.87 (m, 2H); 2.47 (m, 2H); 5.58 (d×d, J$_1$ 16 Hz, J$_2$ 6 Hz, 1H); about 5.55 (m, 1H); 6.30 (d×m, 1H); 8.12 (s, 1H).

MS: 236 (M+, 2), 208 (2), 190 (40), 175 (14), 163 (25), 147 (16), 134 (47), 119 (31), 105 (21), 91 (24), 77 (15), 69 (11), 55 (24), 43 (100).

For the organoleptic evaluation, a 5% solution of the ester in 95% alcohol is prepared and 10 μl thereof are distributed uniform over the entire length of the test cigarettes (American blend made up from Virginia tobacco, Oriental tobacco and Burley tobacco) with the aid of an injection needle and the thus-treated cigarettes are subsequently reconditioned for 24 hours. The same procedure is repeated with 10 μl of 95% alcohol for the production of the corresponding control cigarettes. The panel of experts described the smoke flavour of the test cigarettes as being substantially more typical and more balanced tobacco-like; in addition sweet-flowery nuances were detected.

EXAMPLE 2

A solution of 35.4 g (0.17 mol) of 4-oxo-β-ionol in 20.1 g (0.26 mol) of pyridine is treated at room temperature in the course of 5 minutes with 20.8 g (0.20 mol) of acetic anhydride and the reaction mixture is subsequently stirred at 50° C. for 4 hours. For the working-up, the mixture is cooled to 20° C. treated with 200 ml of hexane, the organic phase is washed in each case twice with water, dilute hydrochloric acid, water, sodium bicarbonate solution and again with water, dried with sodium sulphate and the filtered solution is concentrated.

Distillation of the crude product over a 15 cm Widmer column gives 31.8 g (75%) of >93% 4-oxo-β-ionyl acetate. B.p. 117° C./0.01 mmHg.

IR: 1740, 1670, 1600, 1230, 1095, 1045, 970, 950 cm$^{-1}$.

NMR: 1.17 (2s, 6H); 1.40 (d, J~6.5, 3H); 1.82 (s, 3H); 1.90 (m, 2H); 2.08 (s, 3H); 1.90 (m, 2H); 2.08 (s, 3H); 2.47 (m, 2H); 5.58 (d×d, J$_1$~16 Hz, J$_2$~6 Hz, 1H); 5.55 (m, 1H); 6.28 (d×m, 1H).

MS: 250 (M+, 6), 208 (33), 190 (10), 175 (12), 165 (43), 147 (12), 134 (34), 119 (19), 105 (16), 91 (23), 77 (14), 65 (9), 55 (17), 43 (100).

The panel of experts described the smoke flavour of the test cigarettes produced analogously to Example 1 as being clearly more tobacco-like, flowery and spicy than that of the control cigarettes.

EXAMPLE 3

A solution of 31.2 g (0.15 mol) of 4-oxo-β-ionol in 23.7 g (0.30 mol) of pyridine is treated at room temperature in the course of 5 minutes with 19.5 g (0.15 mol) of propionic anhydride and the reaction mixture is subsequently stirred at 50° C. for 4 hours. The usual working-up (see 4-oxo-β-ionyl acetate) yields 36.8 g of crude product from which there are obtained by distillation over a 10 cm Widmer column 28.9 g (73%) of 4-oxo-β-ionyl propionate (purity>93%). B.p. 132° C./0.05 mmHg.

IR: 1735, 1665, 1600, 1197, 1090, 1050, 980.

MS: 264 (M+, 3); 208 (33), 190 (5), 175 (10), 165 (40), 147 (12), 134 (30), 119 (21), 105 (21), 91 (27), 77 (20), 69 (16), 57 (100), 43 (68).

The panel of experts described the smoke flavour of the test cigarettes manufactured analogously to Example 1 as being sweeter, more hay-like, tobacco-like and considered overall substantially more rounded-off than that of the control cigarettes.

EXAMPLE 4

In a analogous manner from 10.40 g (0.05 mol) of 4-oxo-β-ionol in 7.90 g (0.1 mol) of pyridine and 9.48 g (0.06 mol) of butyric anhydride there are obtained 14.2 g of crude product from which there can be obtained by distillation over a 10 cm Widmer column 9.9 g (71%) of 4-oxo-β-ionyl butyrate (purity>93%). B.p. 140° C./0.05 mmHg.

IR: 1735, 1665, 1600, 1255, 1185, 1100, 1050, 975 cm$^{-1}$.

MS: 278 (M+, 1), 208 (20), 190 (3), 175 (6), 165 (17), 147 (6), 134 (18), 119 (10), 105 (9), 91 (12), 77 (9), 71 (29), 55 (17), 43 (100).

The panel of experts described the smoke flavour of the test cigarettes produced analogously to Example 1 as being substantially more woody, greener and fruity than that of the control cigarettes.

EXAMPLE 5

In an analogous manner from 31.2 g (0.15 mol) of 4-oxo-β-ionol in 23.7 g (0.30 mol) of pyridine and 27.9 g (0.15 mol) of valeric anhydride there are obtained 39.5 g of crude product from which there can be obtained by distillation over a 10 cm Widmer column 30.2 g (69%) of 4-oxo-β-ionyl valerate (purity>92%). B.p. 145°-147° C./0.05 mmHg.

IR: 1735, 1665, 1600, 1255, 1180, 1100, 1050, 980 cm$^{-1}$.

MS: 292 (M+, 1) 208 (49), 190 (5), 175 (11), 165 (44), 147 (13), 134 (38), 119 (20), 109 (20), 91 (28), 85 (31), 77 (19), 69 (21), 57 (89), 43 (86), 41 (100).

The panel of experts described the smoke flavour of the test cigarettes produced analogously to Example 1 as being more clearly reminiscent of dark tobacco and more rounded-off than that of the control cigarettes.

EXAMPLE 6

In an analogous manner from 31.2 g (0.15 mol) of 4-oxo-β-ionol in 23.7 g (0.30 mol) of pyridine and 23.1 g (0.15 mol) of crotonic anhydride there are obtained 41.0 g of crude product from which there be obtained by distillation over a 10 cm Widmer column 30.3 g (73%) of 4-oxo-β-ionyl crotonate (purity>92%). B.p. 140°-141° C./0.05 mmHg.

IR: 1718, 1665, 1600, 1298, 1265, 1188, 1105, 1050, 980 cm$^{-1}$.

MS: 276 (M+, 2), 207 (8), 190 (1), 175 (3), 165 (5), 147 (4), 134 (10), 119 (7), 105 (8), 91 (10), 77 (8), 69 (100), 55 (12), 41 (55).

The panel of experts described the smoke flavour of the test cigarettes produced analogously to Example 1 as being clearly sweeter, more caramel-like and hay-like than that of the control cigarettes.

EXAMPLE 7

A solution of 5.00 g (0.024 mol) of 4-oxo-β-ionol and 2.29 g (0.029 mol) of pyridine in 25 ml of cyclohexane is treated in the course of 10 minutes with a solution of 3.71 g (0.024 mol) of phenylacetyl chloride in 5 ml of cyclohexane. In so doing the temperature of the reaction mixture rises to 35° C. The mixture is subsequently stirred at room temperature for 4 hours, then diluted with 50 ml of ether, the organic phase is washed in each case twice with dilute hydrochloric acid, water, soda solution and again with water dried and concentrated. After evacuation in a high vacuum for two hours there remain behind 7.1 g (91%) of 4-oxo-β-ionyl phenylacetate (purity>90%).

IR: 1735, 1665, 1600, 1500, 1250, 1140, 1040, 965 cm$^{-1}$.

MS: 326 (M+, 8) 208 (78), 193 (16), 190 (15), 175 (14), 165 (96), 147 (18), 137 (28), 134 (38), 121 (30), 109 (30), 91 (100), 77 (20), 69 (23), 55 (35), 43 (83).

The panel of experts described the smoke flavour of the test cigarettes produced analogously to Example 1 as being clearly more hay-like than that of the control cigarettes.

EXAMPLE 8

A solution of 5.00 g (0.024 mol) of 4-oxo-β-ionol and 2.29 g (0.029 mol) of pyridine in 30 ml of cyclohexane is treated in the course of 10 minutes with a solution of 7.11 g (about 0.024 mol) of a mixture consisting of 57% of linolenoyl chloride, 14% of linoleoyl chloride, 18% of oleoyl chloride, 3% of stearoyl chloride and 7% of palmitoyl chloride in 10 ml of cyclohexane. In so doing the temperature of the reaction mixture rises to 40° C. The mixture is subsequently stirred at room temperature for 4 hours, then diluted with 50 ml of ether, the organic phase is washed in each case twice with dilute hydrochloric acid, water, soda solution and again with water, dried and concentrated.

After evacuation in a high vacuum for two hours there remain behind 9.7 g (86%) of product which consists of a mixture of $C_{18}$- and $C_{16}$-fatty acid esters of 4-oxo-β-ionol, namely of about 57% of 4-oxo-β-ionyl linolenate, 14% of 4-oxo-β-ionyl linoleate, 18% of 4-oxo-β-ionyl oleate, 3% of 4-oxo-β-ionyl stearate and 7% of 4-oxo-β-ionyl palmitate.

IR: 1735, 1665, 1600, 1245, 1175, 1095, 1045, 968, 725 cm$^{-1}$.

MS: 277 (24), 208 (59), 192 (58), 191 (36), 175 (11), 165 (22), 147 (18), 134 (20), 121 (27), 109 (22), 95 (38) 79 (48), 67 (58), 55 (72), 43 (64).

The panel of experts described the smoke flavour of the test cigarettes produced analogously to Example 1 as being clearly milder and more rounded-off than that of the control cigarettes. Moreover, a clear "salivating" effect was determined.

The acid chloride mixture used above is obtained by the usual reaction of the corresponding acid mixture, obtainable by saponifying linseed oil with a base, with thionyl chloride.

EXAMPLE 9

Analogously to Example 1, from 5.00 g (0.024 mol) of 4-oxo-dihydro-β-ionol there are obtained 5.1 g of crude product from which there can be obtained by bulb-tube distillation 4.2 g (73.7%) of >93% 4-oxo-dihydro-β-ionyl formate. B.p. about 112° C./0.05 mmHg.

IR: 1720, 1667, 1610, 1182 cm$^{-1}$.

NMR: 1.20 (2s, 6H); 1.37 (d, J 6.5, 3H); 1.80 (s, 3H); 1.60–2.70 (m, 8H); 5.12 (m, J 6.5, 1H); 8.08 (s, 1H).

MS: 238 (M$^+$, 2), 192 (28), 177 (15), 163 (27), 149 (15), 137 (51), 135 (47), 121 (43), 109 (55), 93 (31), 81 (28), 67 (36), 55 (66), 43 (100).

The panel of experts described the smoke flavour of the test cigarettes produced analogously to Example 1 as being clearly more tobacco-like and hay-like than that of the control cigarettes.

EXAMPLE 10

Analogously to Example 2, by reacting 42.3 g (0.20 mol) of 4-oxo-dihydro-β-ionol in 35.4 g (0.45 mol) of pyridine with 30.5 g (0.30 mol) of acetic anhydride they are obtained 47.0 g of crude product from which there can be obtained by distillation over a 15 cm Widmer column 40.3 g (80%) of above 93% 4-oxo-dihydro-β-ionyl acetate. B.p. 120° C./0.1 mmHg.

IR: 1740, 1670, 1610, 1240, 1200, 1134, 1076, 1022, 958, 948 cm$^{-1}$.

NMR: 1.12 (2s, 6H); 1.22 (d, J~6.5, 3H); 1.72 (s, 3H); 1.55–2.55 (m, 8H); 2.02 (s, 3H); 4.91 (m, J~6.5, 1H).

MS: 252 (M$^+$, 1), 192 (100), 177 (34), 163 (93), 149 (19), 135 (49), 121 (60), 107 (24), 93 (19), 55 (19), 43 (48).

The panel of experts described the smoke flavour of the test cigarettes produced analogously to Example 1 as being clearly more tobacco-like, hay-like and sweeter than that of the control cigarettes. Moreover a clear "salivating effect" was determined.

EXAMPLE 11

Analogously to Example 3, by reacting 10.40 g (0.05 mol) of 4-oxo-dihydro-β-ionol in 7.90 g (0.1 mol) of pyridine with 7.80 g (0.06 mol) of propionic anhydride there are obtained 12.5 g of crude product from which there can be obtained by distillation over a 10 cm Widmer column 9.04 g (68%) of above 92% 4-oxo-dihydro-β-ionyl propionate. B.p. 127° C./0.05 mmHg.

IR: 1735, 1665, 1610, 1200, 1140, 1095, 1030 cm$^{-1}$.

MS: 266 (M$^+$, <1), 192 (75), 177 (30), 163 (65), 149 (18), 135 (38), 121 (65), 107 (26), 93 (25), 79 (27), 67 (30), 57 (100), 55 (52), 43 (62), 41 (64).

The panel of experts described the smoke flavour of the test cigarettes produced analogously to Example 1 as being clearly sweeter, more hay-like and considered overall more rounded-off than the flavour of the control cigarettes.

EXAMPLE 12

Analogously to Example 4, by reacting 10.40 g (0.05 mol) of 4-oxo-dihydro-β-ionol in 7.90 g (0.10 mol) of pyridine with 9.48 g (0.06 mol) of butyric anhydride there are obtained 14.0 g of crude product from which there can be obtained by distillation over a 10 cm Widmer column 10.5 g (75%) of above 92% 4-oxo-dihydro-β-ionyl butyrate. B.p. 134°–136° C./0.05 mmHg.

IR: 1735, 1665, 1610, 1260, 1195, 1140, 1095 cm$^{-1}$.

MS: 280 (M$^+$, <1), 192 (60), 177 (24), 163 (51), 149 (14), 135 (25), 121 (43), 107 (17), 93 (17), 79 (16), 71 (28), 55 (33), 43 (100), 41 (57).

The panel of experts described the smoke flavour of the test cigarettes produced analogously to Example 1 as being more fruity and more woody than that of the control cigarettes.

EXAMPLE 13

Analogously to Example 5, from 10.40 g (0.05 mol) of 4-oxo-dihydro-β-ionol 7.90 g (0.10 mol) of pyridine and 11.10 g (0.06 mol) of valeric anhydride there are obtained 14.5 g of crude product from which there can be obtained by distillation 10.3 g (70%) of above 90% 4-oxo-dihydro-β-ionyl valerate. B.p. 138°–139° C./0.05 mmHg.

IR: 1735, 1665, 1610, 1258, 1185, 1140, 1120, 1098 cm$^{-1}$.

MS: 294 (M$^+$, <1), 192 (100), 177 (37), 163 (89), 149 (21), 135 (39), 121 (68), 107 (25), 93 (25), 85 (21), 79 (25), 67 (29), 57 (64), 55 (62), 43 (65), 41 (92).

The panel of expects described the smoke flavour of the test cigarettes produced analogously to Example 1 as being clearly more tobacco-like, flowery, sweeter and rounded-off than that of the control cigarettes.

EXAMPLE 14

Analogously to Example 6 from 10.4 g (0.05 mol) of dihydro-β-ionol 7.90 g (0.10 mol) of pyridine and 9.24 g (0.06 mol) of crotonic anhydride they are obtained 14.5 g of crude product from which there can be obtained by distillation over a 10 cm Widmer column 9.4 g (68%) of >90% 4-oxo-dihydro-β-ionyl crotonate. B.p. 135°–137° C./0.05 mmHg.

IR: 1718, 1665, 1610, 1275, 1195, 1140, 1110, 1115, 980 cm$^{-1}$.

MS: 278 (M$^+$,<1), 192 (49), 177 (20), 163 (40), 149 (12), 135 (23), 121 (51), 107 (21), 93 (22), 79 (22), 69 (100), 55 (38), 43 (44), 41 (85).

The panel of experts described the smoke flavour of the test cigarettes produced analogously to Example 1 as being clearly more spicy and more caramel-like than that of the control cigarettes.

EXAMPLE 15

Analogously to Example 7, from 5.0 g (0.024 mol) of 4-oxo-dihydro-β-ionol, 2.29 g (0.029 mol) of pyridine and 3.71 g (0.024 mol) of phenylacetyl chloride using cyclohexane as the solvent there are obtained 6.13 g (78%) of about 90% 4-oxo-dihydro-β-ionyl phenylacetate.

IR: 1735, 1665, 1605, 1495, 1250, 1130, 1075, 1030, 1010, 960, 765, 720, 700 cm$^{-1}$.

MS: 328 (M$^+$, 2), 192 (100), 177 (24), 163 (67), 149 (14), 137 (30), 135 (33), 121 (43), 109 (21), 91 (92), 81 (16), 67 (17), 55 (29), 43 (24).

The panel of experts described the smoke flavour of the test cigarettes produced analogously to Example 1 as being clearly more hay-like and sweeter than that of the control cigarettes.

EXAMPLE 16

Analogously to Example 8, from 5.0 g (0.024 mol) of 4-oxo-dihydro-β-ionol, 2.29 g (0.029 mol) of pyridine and 7.11 g (about 0.024 mol) of the acid chloride mixture of Example 8 using cyclohexane as the solvent there are obtained 10.5 g (93%) of product which consists of about 57% of 4-oxo-dihydro-β-ionyl linolenate, 14% of 4-oxo-dihydro-β-ionyl linoleate, 18% of 4-oxo-dihydro-β-ionyl oleate, 3% of 4-oxo-dihydro-β-ionyl stearate and 7% of 4-oxo-dihydro-β-ionyl palmitate.

IR: 1735, 1665, 1610, 1245, 1180, 1130, 1080, 1030, 720 cm$^{-1}$.

MS: 470 (M$^+$, 4), 277 (15), 192 (100), 177 (17), 163 (31), 150 (18), 137 (36), 135 (24), 121 (31), 109 (27), 95 (27), 81 (31), 67 (40), 55 (54), 43 (49).

The panel of experts described the smoke flavour of the test cigarettes produced analogously to Example 1 as being clearly milder than that of the control cigarettes, whereby especially the general tobacco impression became intensified advantageously in an objective case. Moreover, a pronounced "salivating effect" was determined.

EXAMPLE 17

Analogously to Example 1, from 1.50 g (7.2 mmol) of 3-oxo-α-ionol there are obtained 1.25 g of crude product from which there can be obtained by bulb-tube distillation 1.00 g of >90% 3-oxo-α-ionyl formate. B.p. about 110° C./0.05 mmHg.

IR: 1720, 1665, 1630, 1250, 1180, 1040, 980, 832 cm$^{-1}$.

MS: 236 (M$^+$, <1), 190 (7), 180 (11), 175 (3), 134 (100), 119 (14), 108 (99), 91 (49), 79 (19), 65 (11), 55 (18), 43 (61).

The panel of experts described the smoke flavour of the test cigarettes produced analogously to Example 1 as being clearly more tobacco-like than that of the control cigarettes.

EXAMPLE 18

Analogously to Example 2, from 4.16 g (0.020 mol) of 3-oxo-α-ionol, 3.16 g (0.040 mol) of pyridine and 3.00 g (0.029 mol) of acetic anhydride there are obtained 4.20 g of crude product from which there can be obtained by bulb-tube distillation 3.50 g (70%) of >93% 3-oxo-α-ionyl acetate. B.p. about 115°-120° C./0.05 mmHg.

IR: 1735, 1665, 1630, 1240, 1150, 1045, 980, 950, 912, 835 cm$^{-1}$.

NMR: 0.96 and 1.03 (in each case s, in each case 3H); 1.32 (d, J=6.5, 3H); 1.90 (s, 3H); 2.03 (s, 3H); 2.20 d, J 5.5, 2H); 2.50 (m, 1H); 5.1-5.7 (2 xm, 3H); 5.90 (s, 1H).

MS: 250 (M$^+$, >1), 190 (9), 175 (6), 148 (5), 134 (50), 119 (9), 108 (70), 91 (25), 87 (8), 79 (10), 65 (5), 55 (8), 43 (100).

The panel of experts described the smoke flavour of the test cigarettes produced analogously to Example 1 as being substantially more tobacco-like than that of the control cigarettes, whereby in the objective case especially a (uniform) intensification of the tobacco impression was determined.

EXAMPLE 19

Analogously to Example 4, from 8.00 g (0.038 mol) of 3-oxo-α-ionol 6.00 g (0.075 mol) of pyridine and 7.20 g (0.045 mol) of butyric anhydride there are obtained 9.5 g of crude product from which there can be obtained by distillation over a 10 cm Widmer column 7.2 g (68%) of 93% 3-oxo-α-ionyl butyrate. B.p. 125°-127° C./mmHg.

IR: 1730, 1670, 1630, 1250, 1185, 1095, 1045, 978 cm$^{-1}$.

MS: 278 (M$^+$, 1), 208 (8), 207 (9), 190 (13), 175 (7), 151 (6), 138 (23), 134 (64), 108 (65), 91 (31), 79 (12), 71 (86), 43 (100).

The panel of experts described the smoke flavour of the test cigarettes produced analogously to Example 1 as being clearly more fruity than in the case of the flavour of the control cigarettes.

EXAMPLE 20

Analogously to Example 5 from 8.00 g (0.038 mol) of 3-oxo-α-ionol, 6.00 g (0.075 mol) of pyridine and 8.38 g (0.045 mol) of valeric anhydride there are obtained 10.1 g of crude product from which there can be obtained by distillation over a 5 cm Widmer column 7.9 g (71%) of >90% 3-oxo-α-ionyl valerate B.p. 130° C./10.1 mmHg.

IR: 1730, 1670, 1630, 1250, 1178, 1045, 980 cm$^{-1}$.

MS: 292 (M$^+$, 2), 236 (3), 222 (5), 207 (18), 190 (20), 175 (11), 148 (7), 134 (99), 108 (96), 91 (54), 85 (100), 79 (20), 57 (62), 43 (50).

The panel of experts described the smoke flavour of the test cigarettes produced analogously to Example 1 as being clearly superior, especially more reminiscent of dark tobacco. Moreover a general intensification of the tobacco impression was determined.

EXAMPLE 21

Analogously to Example 6, from 4.16 g (0.020 mol) of 3-oxo-α-ionol, 3.6 g (0.040 mol) of pyridine and 4.62 g (0.030 mol) of crotonic anhydride there are obtained 4.5 g of crude product from which there can be obtained by bulb-tube distillation 3.8 g (69%) of about 90% 3-oxo-α-ionyl crotonate. B.p. 130° C./0.1 mmHg.

IR: 1720, 1660, 1290, 1185, 1080, 970 cm$^{-1}$.

MS: 276 (M$^+$, 1) 220 (2), 207 (25), 190 (14), 175 (8), 151 (7), 134 (53), 123 (6), 108 (63), 91 (28), 79 (12), 69 (100), 55 (10), 43 (44).

The panel of experts described the smoke flavour of the test cigarettes produced analogously to Example 1 as being superior to that of the control cigarettes, especially as in the former the general tobacco impression became intensified advantageously.

EXAMPLE 22

Analogously to Example 7, from 2.50 g (0.012 mol) of 3-oxo-α-ionol, 1.12 g (0.015 mol) of pyridine and 1.86 g (0.012 mol) of phenylacetyl chloride there are obtained 3.60 g (92%) of about 90% 3-oxo-α-ionyl phenylacetate.

IR: 1730, 1665, 1630, 1600, 1495, 1250, 1140, 1045, 980 730, 700 cm$^{-1}$.

MS: 326 (M$^+$, 1), 207 (4), 191 (26), 175 (5), 149 (8), 137 (26), 135 (41), 118 (34), 107 (14), 91 (100), 79 (9), 65 (13), 55 (10), 43 (19).

The panel of experts described the smoke flavour of the test cigarettes produced analogously to Example 1 as being sweeter and more hay-like than that of the control cigarettes.

EXAMPLE 23

Analogously to Example 8, from 1.50 g (7.2 mmol) of 3-oxo-α-ionol, 0.63 g (8.7 mmol) of pyridine and 2.13 g (about 7.2 mmol) of the acid chloride mixture ex linseed oil there are obtained 2.7 g (82%) of product which consists of about 57% of 3-oxo-α-ionyl linolenate, 14% of 3-oxo-α-ionyl linoleate 18% of 3-oxo-α-ionyl oleate, 3% of 3-oxo-α-ionyl stearate and 7% of 3-oxo-α-ionyl palmitate.

IR: 1735, 1670, 1635, 1245 1175, 1045, 970, 720 cm$^{-1}$.

MS: 468 (M+, <1), 277 (35), 207 (15), 192 (100), 177 (24), 149 (25), 137 (68), 135 (94), 123 (34), 108 (38), 91 (49), 83 (58), 67 (57), 55 (82), 43 (55).

The panel of experts described the smoke flavour of the test cigarettes produced analogously to Example 1 as being milder than that of the control cigarettes. Moreover, a pleasant "salivating effect" was determined.

EXAMPLE 24

Analogously to Example 2 from 1.50 g (7.1 mmol) of 3-oxo-dihydro-α-ionol, 1.12 g (14.2 mmol) of pyridine and 0. 87 g (8.6 mmol) of acetic anhydride there are obtained 1.60 g of crude product from which there can be obtained by bulb-tube distillation 1.15 g (65%) of about 90% 3-oxo-dihydro-α-ionyl acetate. B.p. about 115° C./0.05 mmHg.

IR: 1735, 1665, 1630, 1242, 1132, 1074, 1022, 950 cm$^{-1}$.

NMR: 1.07 and 1.10 (in each case s, in each case 3H); 1.27 (d, J 6.5, 3H); 2.05 (s, 3H), 2.07 (s, 3H); 1.50–2.62 (m, 7H); 4.90 (m, 1H); 5.84 (s, 1H).

MS: 252 (M+, 3), 209 (1), 192 (4), 177 (9), 163 (3), 150 (10), 138 (12), 135 (20), 123 (13), 121 (15), 108 (32), 93 (23), 79 (10), 67 (15), 55 (16), 43 (100).

The panel of experts described the smoke flavour of the test cigarettes produced analogously to Example 1 as being more rounded-off than that of the control cigarettes; at the same time the general tobacco impression was intensified perceptibly.

EXAMPLE 25

Analogously to Example 5, from 1.50 g (7.1 mmol) of 3-oxo-dihydro-α-ionol, 1.12 g (14.2 mmol) of pyridine and 1.60 g (8.6 mmol) of valeric anhydride there are obtained 1.95 g of crude product from which there can be obtained by bulb-tube distillation 1.44 g (69%) of about 90% 3-oxo-dihydro-α-ionyl valerate. B.p. about 130° C./0.05 mmHg.

IR: 1730, 1665, 1630, 1250, 1180, 1132 cm$^{-1}$.

MS: 294 (M+, 16), 209 (30), 192 (27), 177 (45), 163 (16), 150 (55), 138 (59), 135 (88), 123 (52), 12 (49), 108 (100), 93 (64), 85 (55), 79 (28), 67 (46), 57 (75), 41 (80).

The panel of experts described the smoke flavour of the test cigarettes produced analogously to Example 1 as being more reminiscent of oriental tobacco than that of the control cigarettes.

EXAMPLE 26

Analogously to Example 7, from 1.70 g (8.1 mmol) of 3-oxo-dihydro-α-ionol, 7.90 g (10 mmol) of pyridine and 1.25 g (8.1 mmol) of phenylacetyl chloride there are obtained 2.22 g (84%) of about 90% 3-oxo-dihydro-α-ionyl phenylacetate.

IR: 1730, 1665, 1630, 1600, 1495, 1250, 1162, 1130, 1085, 725, 700 cm$^{-1}$.

MS: 328 (M+, 30), 209 (7), 193 (56), 177 (16), 163 (8), 151 (34), 135 (42), 118 (39), 109 (58), 91 (100), 79 (14), 67 (31), 55 (22), 41 (25).

The panel of experts described the smoke flavour of the test cigarettes produced analogously to Example 1 as being sweeter and more hay-like than that of the control cigarettes.

EXAMPLE 27

Analogously to Example 8, from 1.05 g (5.0 g (5.0 mmol) of 3-oxo-dihydro-α-ionol, 0.55 g (7.0 mmol) of pyridine and 1.48 g (about 5 mmol) of the acid chloride mixture ex linseed oil there are obtained 2.0 g (85%) of product which consists of about 57% of 3-oxo-dihydro-α-ionyl linolenate, 14% of 3-oxo-dihydro-α-ionyl linoleate, 18% of 3-oxo-dihydro-α-ionyl oleate, 3% of 3-oxo-dihydro-α-ionyl stearate and 7% of 3-oxo-dihydro-α-ionyl palmitate.

IR: 1730, 1665, 1630, 1250, 1180, 1130, 725 cm$^{-1}$.

MS: 470 (3), 277 (17), 209 (32), 193 (84), 177 (22), 151 138 (55), 135 (69), 123 (39), 109 (100), 95 (43), (38), 67 (68), 55 (62), 43 (54).

The panel of experts described the smoke flavor of the test cigarettes produced analogously to Example 1 as being milder and more balanced than that of the control cigarettes.

EXAMPLE 28

A comparison was made between the esters of formula 1 and the esters of Japanese Patent Publication No. 57 734 (Japan Tobacco and Salt Pub., of 20th May 1981, filed on 16th October 1979) which have the general formula:

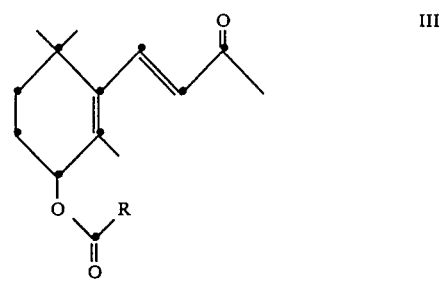

III

For comparative purposes the formate, acetate, propionate, n-butyrate, n-valerate, 2-methylbutyrate and crotonate were prepared, i.e. R in formula 111=H, —CH$_3$, —CH$_2$CH$_3$, —CH$_2$CH$_2$CH$_3$, —(CH$_2$)$_3$CH$_3$, —CH(CH$_3$)—CH$_3$, —CH=CH—CH$_3$.

In a manner as described in Example 1, test cigarettes were prepared incorporating as a flavorant the known esters of formula III described above. These cigarettes were compared with test cigarettes that had been flavored with the corresponding esters of formula I, i.e. the esters of this invention.

As was set forth earlier, the cigarettes flavored with esters of formula I had clearly improved smoke characteristics, the general tobacco impression being intensified and the total flavor appearing more rounded and more full. The cigarettes flavored with the esters of formula III, however, were clearly characterized by perfumistic strongly flowery notes.

This excessive perfuming of cigarettes was, however, not desirable in the present case. The objective in the present case was to bring into play a full, non-perfumed tobacco character in the flavor of the smoke, an objective which is now of extraordinary importance for the large number of smokers who prefer cigarettes with low nicotine content (light cigarettes, lights, low-delivery cigarettes, low tar cigarettes), since this low nicotine content is achieved for the most part by means of a so-called high-retention filter and/or ventilation, such techniques being known, for the most part to significantly impair the tobacco flavor.

The pronounced perfuming of cigarettes, which may be justified in the case of certain tobacco mixtures, is of far less significance in the present case.

I claim:

1. A method for improving, enhancing or modifying the organoleptic properties of a tobacco product which comprises adding thereto an effective amount of a compound of the formula

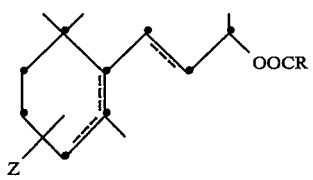

wherein:
RCO represents an acyl group containing from one to eighteen carbon atoms,
the dotted line in the side-chain represents an optional bond,
one of the dotted lines in the ring represents an additional bond, and,
Z represents an oxo group which is in the position α to the double bond in the ring.

2. A method according to claim 1 wherein RCO represents
formyl,
an alkanoyl group containing from two to eighteen carbon atoms, or,
an alkenyl group containing from three to eighteen carbon atoms.

3. A method according to claim 2 wherein there is added a compound of the formula

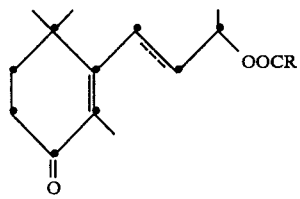

and RCO contains from one to five carbon atoms.

4. A method according to claim 3 wherein the compound is selected from the group consisting of
4-(2,6,6-trimethyl-3-oxocyclohex-1-en-1-yl)but-3-en-2-yl valerate,
4-(2,6,6-trimethyl-3-oxocyclohex-1-en-1-yl)but-3-en-2-yl isovalerate,
4-(2,6,6-trimethyl-3-oxocyclohex-1-en-1-yl)but-3-en-2-yl butyrate,
4-(2,6,6-trimethyl-3-oxocyclohex-1-en-1-yl)but-3-en-2-yl acetate,
4-(2,6,6-trimethyl-3-oxocyclohex-1-en-1-yl)but-3-en-2-yl formate,
4-(2,6,6-trimethyl-3-oxocyclohex-1-en-1-yl)but-3-en-2-yl crotonate,
4-(2,6,6-trimethyl-3-oxocyclohex-1-en-1-yl)but-2-yl valerate,
4-(2,6,6-trimethyl-3-oxocyclohex-1-en-1-yl)but-2-yl acetate.

5. A method according to claim 4 wherein the compound is selected from the group consisting of 4-(2,6,6-trimethyl-3-oxocyclohex-1-en-1-yl)but-3-en-2-yl valerate and 4-(2,6,6-trimethyl-3-oxocyclohex-1-en-1-yl)but-3-en-2-yl acetate.

6. A method according to claim 2 wherein the compound is 4-(2,6,6-trimethyl-4-oxocyclohex-2-en-1-yl)but-3-en-2-yl valerate.

7. A tobacco product to which there has been added a compound of formula 1, in an amount effective to modify the organoleptic properties of said tobacco, said compound having the structure

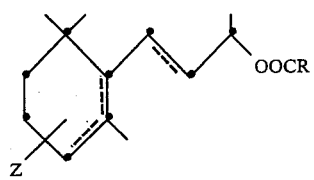

wherein:
RCO represents an acyl group containing from one to eighteen carbon atoms,
the dotted line in the side-chain represents an optional bond,
one of the dotted lines in the ring represents an additional bond, and,
Z represents an oxo group which is in the position to the double bond in the ring.

8. A tobacco product according to claim 7 wherein RCO represents
formyl,
an alkanoyl group containing from two to eighteen carbon atoms, or,
an alkanoyl group containing from three to eighteen carbon atoms.

9. A tobacco product according to claim 8 wherein there is added a compound of the formula

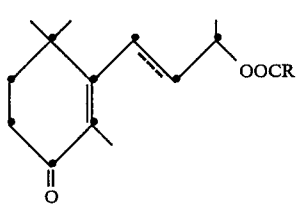

and RCO contains from one to five carbon atoms.

10. A tobacco product according to claim 9 wherein the compound is selected from the group consisting of
4-(2,6,6-trimethyl-3-oxocyclohex-1-en-1-yl)but-3-en-2-yl valerate,
4-(2,6,6-trimethyl-3-oxocyclohex-1-en-1-yl)but-3-en-2-yl isovalerate,
4-(2,6,6-trimethyl-3-oxocyclohex-1-en-1-yl)but-3-en-2-yl butyrate, 4-(2,6,6-trimethyl-3-oxocyclohex-1-en-1-yl)but-3-en-2-yl acetate, 4-(2,6,6-trimethyl-3-oxocyclohex-1-en-1-yl)but-3-en-2-yl formate, 4-(2,6,6-trimethyl-3-oxocyclohex-1-en-1-yl)but-3-en-2-yl crotonate, 4-(2,6,6-trimethyl-3-oxocyclohex-1-en-1-yl)but-2-yl valerate, 4-(2,6,6-trimethyl-3-oxocyclohex-1-en-1-yl)but-2-yl acetate.

11. A tobacco product according to claim 10 wherein the compound is selected from the group consisting of 4-(2,6,6-trimethyl-3-oxocyclohex-1-en-1-yl)but-3-en-2-yl valerate and 4-(2,6,6-trimethyl-3-oxocyclohex-1-en-1-yl)but-3-en-2-yl acetate.

12. A tobacco product according to claim 8 wherein the compound is 4-(2,6,6-trimethyl-4-oxocyclohex-2-en-1-yl)but-3-en-2-yl valerate.

13. A composition for flavoring tobacco which comprises an amount of a compound of formula 1, effective to modify the organoleptic properties of said tobacco, said compound having the structure

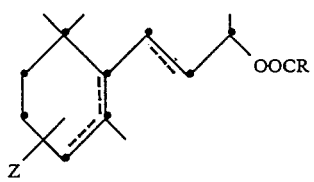   I wherein:
RCO represents an acyl group containing from one to eighteen carbon atoms,
the dotted line in the side-chain represents an optional bond,
one of the dotted lines in the ring represents an additional bond, and,
Z represents an oxo group which is in the position to the double bond in the ring,
and at least one other tobacco flavoring agent.

14. A composition according to claim 13 wherein RCO represents formyl,
an alkanoyl group containing from two to eighteen carbon atoms, or,
an alkanoyl group containing from three to eighteen carbon atoms.

15. A composition according to the claim 14 wherein there is added a compound of the formula

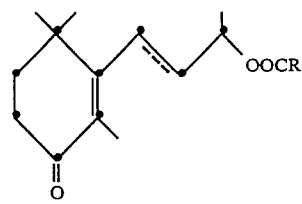   Ia and RCO contains from one to five carbon atoms.

16. A composition according to claim 15 wherein the compound is selected from the group consisting of 4-(2,6,6-trimethyl-3-oxocyclohex-1-en-1-yl)but-3-en-2-yl valerate, 4-(2,6,6-trimethyl-3-oxocyclohex-1-en-1-yl)but-3-en-2-yl isovalerate, 4-(2,6,6-trimethyl-3-oxocyclohex-1-en-1-yl)but-3-en-2-yl butyrate, 4-(2,6,6-trimethyl-3-oxocyclohex-1-en-1-yl)but-3-en-2-yl acetate, 4-(2,6,6-trimethyl-3-oxocyclohex-1-en-1-yl)but-3-en-2-yl formate, 4-(2,6,6-trimethyl-3-oxocyclohex-1-en-1-yl)but-3-en-2-yl crotonate, 4-(2,6,6-trimethyl-3-oxocyclohex-1-en-1-yl)but-2-yl valerate, 4-(2,6,6-trimethyl-3-oxocyclohex-1-en-1-yl)but-2-yl acetate.

17. A composition according to claim 16 wherein the compound is selected from the group consisting of 4-(2,6,6-trimethyl-3-oxocyclohex-1-en-1-yl)but-3-en-2-yl valerate and 4-(2,6,6-trimethyl-3-oxocyclohex-1-en-1-yl)but-3-en-2-yl acetate.

18. A composition according to claim 14 wherein the compound is 4-(2,6,6-trimethyl-4-oxocyclohex-2-en-1-yl)but-3-en-2-yl valerate.

* * * * *

UNITED STATES PATENT AND TRADEMARK OFFICE
CERTIFICATE OF CORRECTION

PATENT NO. : 4,963,193

DATED : October 16, 1990

INVENTOR(S) : Roman Kaiser

It is certified that error appears in the above-identified patent and that said Letters Patent is hereby corrected as shown below:

At column 2, line 49, correct "3-oxo-ß-ionyl valerate" to read --3-oxo-$\alpha$-ionyl valerate--.

At column 15, claim 13, line 41, correct "position to" to read --position $\alpha$ to--.

Signed and Sealed this

Seventeenth Day of March, 1992

Attest:

HARRY F. MANBECK, JR.

*Attesting Officer*  *Commissioner of Patents and Trademarks*